United States Patent
Bruns

(10) Patent No.: US 8,380,309 B2
(45) Date of Patent: Feb. 19, 2013

(54) METHOD AND APPARATUS TO OPTIMIZE PACING HEART RATE

(75) Inventor: Hans-Juergen Bruns, Muenster (DE)

(73) Assignee: Medtronic, Inc., Minneapolis, MN (US)

( * ) Notice: Subject to any disclaimer, the term of this patent is extended or adjusted under 35 U.S.C. 154(b) by 898 days.

(21) Appl. No.: 12/262,888

(22) Filed: Oct. 31, 2008

(65) Prior Publication Data

US 2010/0082077 A1  Apr. 1, 2010

Related U.S. Application Data

(60) Provisional application No. 61/101,655, filed on Sep. 30, 2008.

(51) Int. Cl.
*A61N 1/00* (2006.01)
*A61B 5/04* (2006.01)

(52) U.S. Cl. .......... 607/18; 607/119; 600/509; 600/511; 600/513

(58) Field of Classification Search .................... 607/18, 607/119; 600/509, 511, 513
See application file for complete search history.

(56) References Cited

U.S. PATENT DOCUMENTS

| | | | |
|---|---|---|---|
| 6,438,408 B1 * | 8/2002 | Mulligan et al. | 600/510 |
| 6,915,160 B2 | 7/2005 | Auricchio et al. | |
| 7,027,866 B2 | 4/2006 | Warkentin | |
| 2004/0019365 A1 | 1/2004 | Ding et al. | |
| 2005/0096705 A1 | 5/2005 | Pastore et al. | |
| 2005/0154422 A1 | 7/2005 | Band et al. | |
| 2006/0173248 A1 | 8/2006 | Karamanoglu et al. | |
| 2006/0224204 A1 | 10/2006 | Hettrick et al. | |
| 2007/0156057 A1 | 7/2007 | Cho et al. | |

FOREIGN PATENT DOCUMENTS

| WO | WO 02/053228 A1 | 7/2002 |
|---|---|---|
| WO | WO02053228 * | 7/2002 |
| WO | WO 2005/035046 A2 | 4/2005 |

OTHER PUBLICATIONS (PCT/US2009/057124) PCT Notification of Transmittal of the International Search Report and the Written Opinion of the International Searching Authority.

* cited by examiner

*Primary Examiner* — Nicole F Lavert
(74) *Attorney, Agent, or Firm* — Reed A. Duthler; Stephen W. Bauer

(57) ABSTRACT

The present disclosure provides an apparatus and method of optimizing a pacing heart rate. The method can include obtaining a preload-frequency relation and a force-frequency relation from histogram data for a patient condition and determining an optimal pacing heart rate for the patient condition. The optimal pacing heart rate can be substantially between a first heart rate corresponding to a minimum preload condition based on the preload-frequency relation and a second heart rate corresponding to a sustained ionotropic reserve condition based on the force-frequency relation.

11 Claims, 11 Drawing Sheets

METHOD AND APPARATUS TO OPTIMIZE PACING HEART RATE

RELATED APPLICATION

This application claims the benefit of and priority to U.S. Provisional Application Ser. No. 61/101,655, filed Sep. 30, 2008, entitled, "Method and Apparatus to Optimize Pacing Heart Rate," the contents of which are incorporated by reference herein in its entirety.

TECHNICAL FIELD

This disclosure relates generally to a method and apparatus to optimize pacing heart rates.

BACKGROUND

Pacing therapy can be used in the treatment of heart failure, which refers to a clinical syndrome in which an abnormality of cardiac function causes a below normal cardiac output that can fall below a level adequate to meet the metabolic demand of peripheral tissues. When uncompensated, it usually presents as congestive heart failure due to the accompanying venous and pulmonary congestion. It has been shown that some heart failure patients suffer from intraventricular and/or interventricular conduction defects (e.g., bundle branch blocks) such that their cardiac outputs can be increased by improving the synchronization of ventricular contractions with electrical stimulation. Cardiac rhythm management devices have therefore been developed which provide electrical stimulation to the ventricles in an attempt to improve the coordination of cardiac contractions, termed cardiac resynchronization therapy (CRT).

The degree to which a heart muscle fiber is stretched before it contracts is termed the preload, while the degree of tension or stress on a heart muscle fiber as it contracts is termed the afterload. When a myocardial region contracts late relative to other regions, the contraction of those other regions stretches the later contracting region and increases its preloading, thus causing an increase in the contractile force generated by the region. Because pressure within the ventricles rises rapidly from a diastolic to a systolic value as blood is pumped out into the aorta and pulmonary arteries, the parts of the ventricles that contract later during systole do so against a higher afterload than do parts of the ventricles contracting earlier. Thus, a ventricular region that contracts later than other regions is subjected to both an increased preload and afterload, both of which act to increase the mechanical stress experienced by the region relative to other regions.

Resynchronization pacing may be delivered in a manner that pre-excites one or more hypertrophied regions in order to subject the regions to a lessened preload and afterload. For example, the ventricles may be paced at multiple sites using a multi-site resynchronization pacing mode, where the delivery of paces to multiple ventricular sites during a cardiac cycle is used to not only enforce a minimum ventricular heart rate, but also to alter the depolarization patterns of the ventricles during systole and improve the coordination of the ventricular contraction. The pulse output sequence can be specified so that one or more hypertrophied regions are paced before other regions during systole and hence mechanically unloaded. By unloading such hypertrophied regions in this way over a period of time, reversal of undesirable ventricular remodeling is effected.

Implantable medical devices have been developed that provide appropriately timed electrical stimulation to one or more heart chambers in an attempt to improve the coordination of ventricular contractions during CRT. Ventricular resynchronization is useful in treating heart failure because resynchronization results in a more coordinated contraction of the ventricles with improved pumping efficiency and increased cardiac output. Currently, a common form of CRT applies stimulation pulses to both ventricles, either simultaneously or separated by a specified biventricular offset interval, and after a specified atrio-ventricular delay interval with respect to the detection of an intrinsic atrial contraction.

In summary, current optimization strategies in cardiac pacing aim to ensure an optimal loading of the ventricles (e.g., atrio-ventricular delay optimization). Also in CRT, an interventricular optimization can lead to an improved cardiac performance as measured by left ventricular pressure gradient.

SUMMARY

In one or more embodiments, an apparatus and method is provided for optimizing a pacing heart rate. The method can include obtaining a preload-frequency relation and a force-frequency relation from a histogram for a patient condition and determining an optimal pacing heart rate for the patient condition. The optimal pacing heart rate can be substantially between a first heart rate corresponding to a minimum preload condition based on the preload-frequency relation and a second heart rate corresponding to a sustained ionotropic reserve condition based on the force-frequency relation.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

The present disclosure describes a method and apparatus to optimize a pacing heart rate or to diagnose exercise tolerance and other cardiovascular disease state indicators using algorithms combining physiological measures and including hemodynamic sensor information. The present disclosure also describes a method of optimizing a pacing heart rate for cardiac resynchronization therapy (CRT) by an implantable medical device (IMD) that measures and analyzes right ventricle diastolic pressure (RVDP).

The following detailed description is merely illustrative only and is not intended to limit the application and uses of the present disclosure. Furthermore, there is no intention to be bound by any expressed or implied theory presented in the preceding technical field, background, brief summary or the following detailed description.

The invention may be described herein in terms of functional and/or logical block components and various processing steps. It should be appreciated that such block components may be realized by any number of hardware, software, and/or firmware components configured to perform the specified functions. For example, an embodiment may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that the present disclosure may be practiced in conjunction with any number of medical devices and therapies and that the system described herein is merely one exemplary application.

For the sake of brevity, conventional techniques related to IMD sensor signal processing, RVDP sensing, the adjustment and control of IMD therapy signals, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

Figure 4:
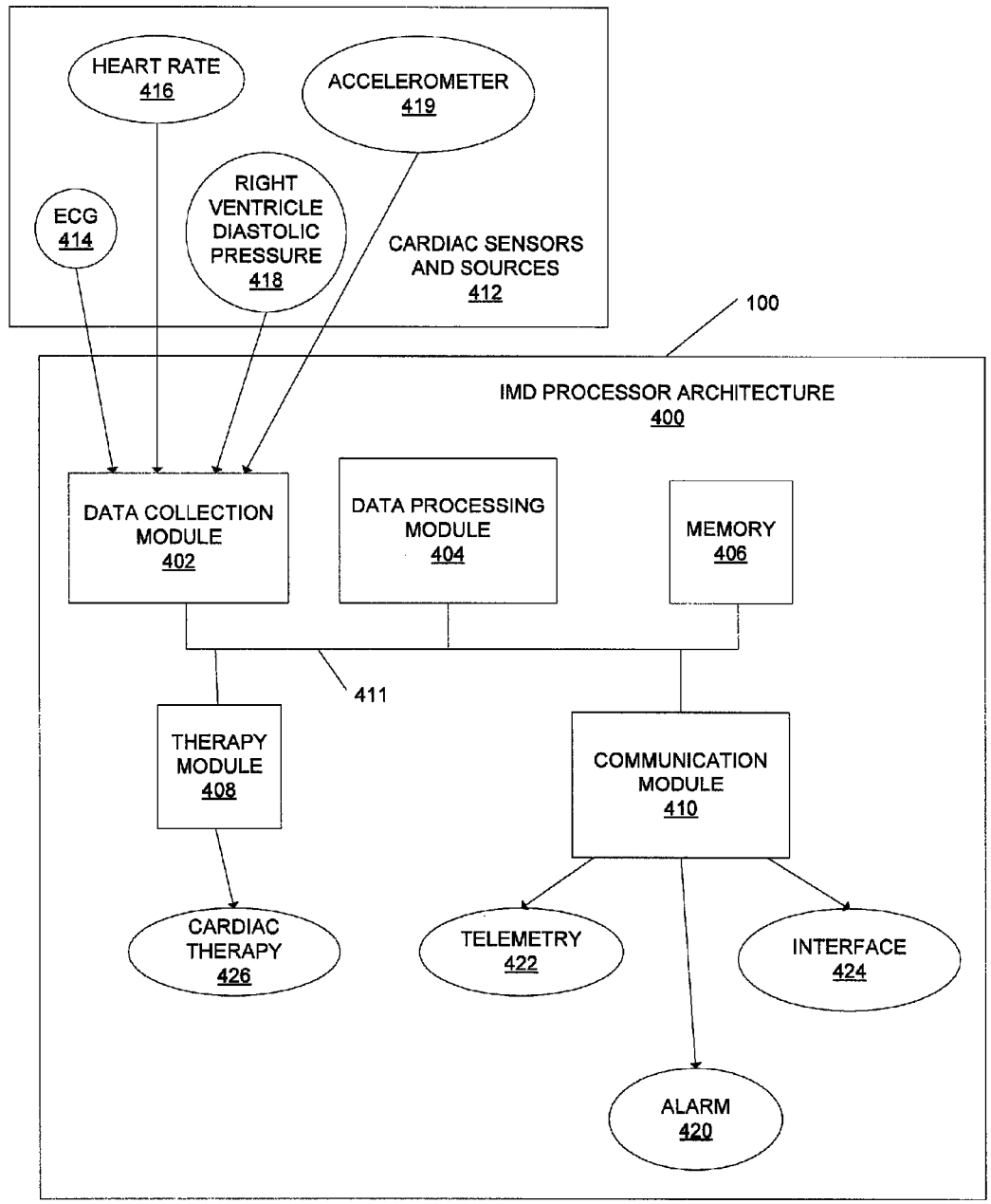
FIG. 4 is a schematic representation of a portion of an IMD configured in accordance with an embodiment of the present disclosure.

The following description refers to elements or features being "connected" or "coupled" together. As used herein, unless expressly stated otherwise, "connected" means that one element/feature is directly or indirectly connected to another element/feature, and not necessarily mechanically. Likewise, unless expressly stated otherwise, "coupled" means that one element/feature is directly or indirectly coupled to another element/feature, and not necessarily mechanically. Thus, although the schematic shown in FIG. 4 depicts one example arrangement of processing elements, additional intervening elements, devices, features, or components may be present in an actual embodiment (assuming that the functionality of the system is not adversely affected).

In connection with the operation of an IMD, implantable sensors may be expected to provide diagnostic data to the IMD and/or to facilitate automated feedback control of the IMD. For example, direct measurement of RVDP may be well suited to monitor ventricular preload. It would also be useful, however, if the same implantable RVDP sensor could be used to optimize device timing. In this regard, an example embodiment incorporates real-time RVDP signals for use as feedback control (preferably closed loop, but also applicable to open loop) of IMD settings or operational parameters.

Figure 1:
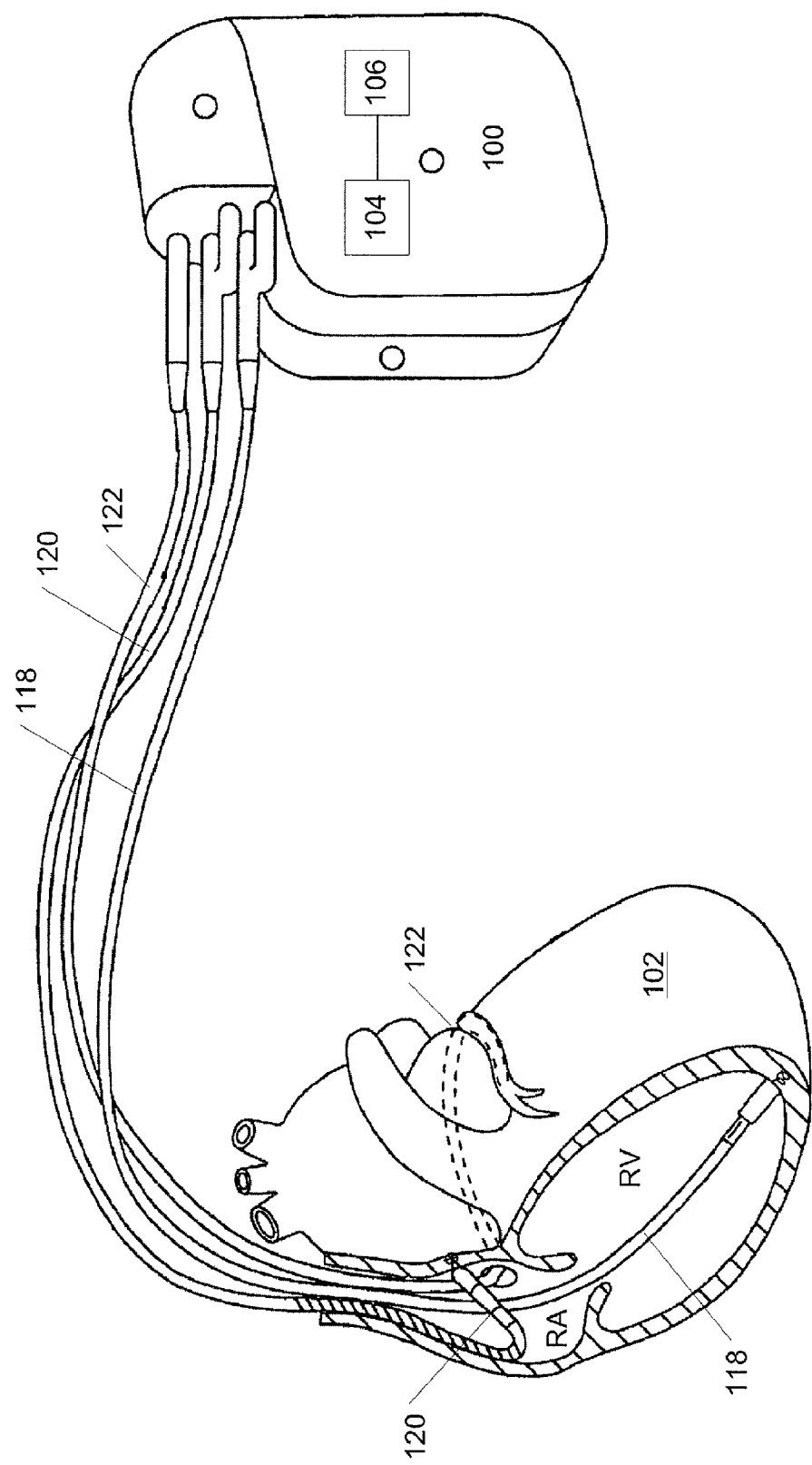
FIG. 1 is a schematic diagram of an implantable medical device in accordance with an embodiment of the present disclosure.

FIG. 1 is an illustration of an exemplary implantable medical device (IMD) 100 connected to monitor a patient's heart 102. IMD 100 may be configured to integrate both monitoring and therapy features, as will be described below. IMD 100 collects and processes data about heart 102 from one or more sensors including a pressure sensor and an electrode pair for sensing cardiac electrogram (EGM) signals. IMD 100 may further provide therapy or other response to the patient as appropriate, and as described more fully below. As shown in FIG. 1, IMD 100 may be generally flat and thin to permit subcutaneous implantation within a human body, e.g., within upper thoracic regions or the lower abdominal region. IMD 100 is provided with a hermetically-sealed housing that encloses a processor 104, a digital memory 106, and other components as appropriate to produce the desired functionalities of the device. In various embodiments, IMD 100 is implemented as any implanted medical device capable of measuring the heart rate of a patient and a ventricular or arterial pressure signal, including, but not limited to a pacemaker, defibrillator, electrocardiogram monitor, blood pressure monitor, drug pump, insulin monitor, or neurostimulator. In some embodiments, the IMD 100 can be a pacemaker system including a hemodynamic sensor together with memory function and software download capability for optimization algorithms. An example of a suitable IMD that may be used in various exemplary embodiments is the CHRONICLE® monitoring device available from Medtronic, Inc. of Minneapolis, Minn., which includes a mechanical sensor capable of detecting a pressure signal. In a further embodiment, IMD 100 is any device that is capable of sensing a pressure signal and providing pacing and/or defibrillation or other electrical stimulation therapies to the heart. Another example of an IMD capable of sensing pressure-related parameters is described in commonly assigned U.S. Pat. No. 6,438,408B1 issued to Mulligan et al. on Aug. 20, 2002.

Processor 104 may be implemented with any type of microprocessor, digital signal processor, application specific integrated circuit (ASIC), field programmable gate array (FPGA) or other integrated or discrete logic circuitry programmed or otherwise configured to provide functionality as described herein. Processor 104 executes instructions stored in digital memory 106 to provide functionality as described below. Instructions provided to processor 104 may be executed in any manner, using any data structures, architecture, programming language and/or other techniques. Digital memory 106 is any storage medium capable of maintaining digital data and instructions provided to processor 104 such as a static or dynamic random access memory (RAM), or any other electronic, magnetic, optical or other storage medium.

As further shown in FIG. 1, IMD 100 may receive one or more cardiac leads for connection to circuitry enclosed within the housing. In the example of FIG. 1, IMD 100 receives a right ventricular endocardial lead 118, a left ventricular coronary sinus lead 122, and a right atrial endocardial lead 120, although the particular cardiac leads used will vary from embodiment to embodiment. In addition, the housing of IMD 100 may function as an electrode, along with other electrodes that may be provided at various locations on the housing of IMD 100. In alternate embodiments, other data inputs, leads, electrodes and the like may be provided. Ventricular leads 118 and 122 may include, for example, pacing electrodes and defibrillation coil electrodes (not shown) in the event IMD 100 is configured to provide pacing, cardioversion and/or defibrillation. In addition, ventricular leads 118 and 122 may deliver pacing stimuli in a coordinated fashion to provide biventricular pacing, cardiac resynchronization, extra systolic stimulation therapy or other therapies.

IMD 100 suitably collects and processes data about heart 102 from one or more sources (e.g., RVDP sensor, heart rate monitor, blood pressure monitor, electrocardiogram (ECG) waveform, electrogram waveform (EGM), etc.). IMD 100 obtains pressure data input from a pressure sensor that is carried by a lead, such as right ventricular endocardial lead 118. The right ventricular lead 118 can provide a real-time RVDP signal to IMD 100 from the right ventricle of heart 120. The RVDP sensor may be contained on an independent lead, or may be integrated into a pacing or defibrillation lead. In alternate embodiments, other data inputs, leads, electrodes and the like may be provided. The right ventricular lead 118 may include, for example, pacing electrodes and defibrillation coil electrodes (not shown) for purposes of pacing, cardioversion, and/or defibrillation. IMD 100 may also obtain input data from other internal or external sources (not shown) such as an oxygen sensor, pH monitor, accelerometer or the like.

In operation, IMD 100 obtains data about the heart 102 via the leads 118, 120, 122, and/or other sources. This data is provided to processor 104, which suitably analyzes the data, stores appropriate data in memory 106, and/or provides a response or report as appropriate. In particular, IMD 100 generates one or more therapy signals that are preferably optimized in accordance with the obtained data. In the example embodiment, IMD 100 selects or adjusts an optimized pacing heart rate and coordinates the delivery of the optimized pacing heart rate by IMD 100 or another appropriate device.

Any identified cardiac episodes (e.g. an arrhythmia or heart failure decompensation) can be treated by intervention of a physician or in an automated manner. In various embodiments, IMD 100 activates an alarm upon detection of a cardiac event. Alternatively or in addition to alarm activation, IMD 100 selects or adjusts a therapy and coordinates the delivery of the therapy by IMD 100 or another appropriate device. Optional therapies that may be applied in various embodiments may include drug delivery or electrical stimulation therapies such as cardiac pacing, CRT, extra systolic stimulation, and neurostimulation.

Figure 2:
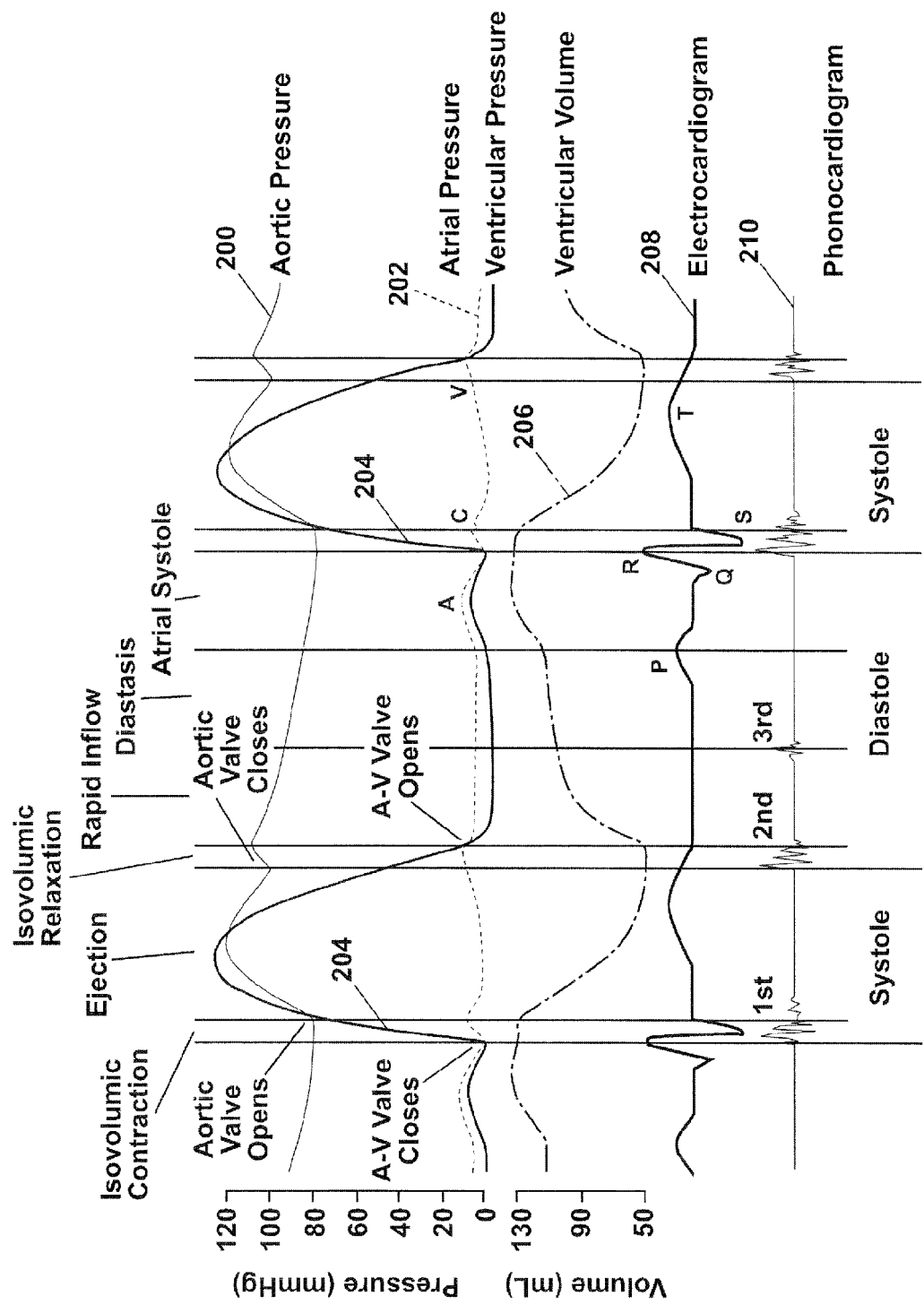
FIG. 2 is a diagram of pressures and volumes for two cardiac cycles.

FIG. 2 is a diagram illustrating changes in aortic pressure 200, atrial pressure 202, ventricular pressure 204, and ventricular volume 206 as related in time to an electrocardiogram 208 and a phonocardiogram 210 for two cardiac cycles. Each cardiac cycle is divided into diastole, which represents ventricular filling, and systole, which represents contraction and ejection of blood from the ventricles. In some embodiments, RVDP can be measured by right ventricular lead 118 during diastole when the right ventricle is being filled and preloaded.

Figure 3:
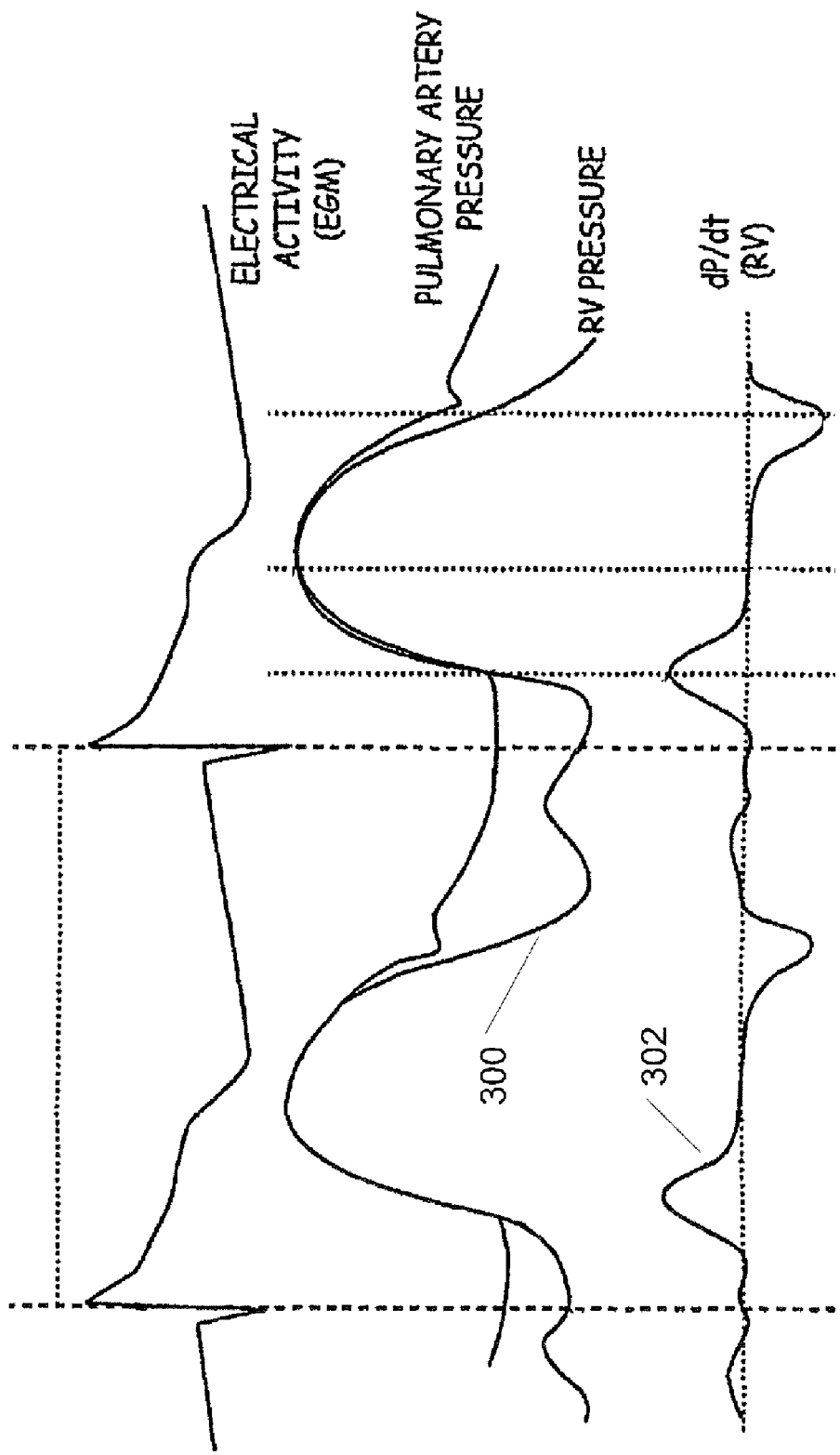
FIG. 3 is a diagram of right ventricular diastolic pressure (RVDP) and the first derivative of right ventricular diastolic pressure (RV dP/dt) for two cardiac cycles.

FIG. 3 is a diagram showing an example graph of a RVDP signal 300 along with an example graph of a secondary signal 302 that represents the first derivative of the RVDP signal (i.e., the RV dP/dt signal). It should be appreciated that these graphs are merely examples and that the actual RVDP characteristics will vary from patient to patient, vary according to the current patient condition, and vary over time.

FIG. 4 is a schematic representation of a portion of an IMD 100 configured in accordance with an example embodiment of the present disclosure. In particular, FIG. 4 depicts an exemplary data processing layout for an IMD processor architecture 400, which may be located within the housing of a suitable IMD as described herein. In this example, processor architecture 400 includes at least a data collection module 402, a data processing module 404, a suitable amount of memory 406, a therapy module 408, and/or a communication module 410. These modules may be coupled to each other via a suitable data communication bus or arrangement 411. Each of the various modules may be implemented with computer-executable instructions stored in memory 406 and executing on processor architecture 400, or in any other practical manner. The exemplary modules and blocks shown in FIG. 4 are intended to illustrate one logical model for implementing an IMD in accordance with the invention, and should not be construed as limiting. Indeed, the various practical embodiments may have widely varying software modules, data structures, applications, processes and the like. As such, the various functions of each module may in practice be combined, augmented, optimized or otherwise differently-organized in any fashion.

In accordance with the practices of persons skilled in the art of computer programming, the present disclosure may be described herein with reference to symbolic representations of operations that may be performed by the various computing components, modules, or devices. Such operations are sometimes referred to as being computer-executed, computerized, software-implemented, or computer-implemented. It will be appreciated that operations that are symbolically represented include the manipulation by the various microprocessor devices of electrical signals representing data bits at memory locations in the system memory, as well as other processing of signals. The memory locations where data bits are maintained are physical locations that have particular electrical, magnetic, optical, or organic properties corresponding to the data bits.

When implemented in software or firmware, various elements of the IMDs described herein are essentially the code segments or instructions that perform the various tasks. The program or code segments can be stored in a processor-readable medium or transmitted by a computer data signal embodied in a carrier wave over a transmission medium or communication path. The "processor-readable medium" or "machine-readable medium" may include any medium that can store or transfer information. Examples of the processor-readable medium include an electronic circuit, a semiconductor memory device, a ROM, a flash memory, an erasable ROM (EROM), a hard disk, a fiber optic medium, or the like. The computer data signal may include any signal that can propagate over a transmission medium such as electronic network channels, optical fibers, air, electromagnetic paths, or RF links.

Data collection module 402 suitably interacts with one or more data sources 412 to obtain data about the patient. Data sources 412 include any source of information about the patient's heart and possibly other physiologic information. In various embodiments, data sources 412 may include an ECG source 414 that provides electrical impulses or other observed signals that can be used to model the patient's ECG waveform. Other data sources 412 may include a heart rate sensor 416, a RVDP sensor or monitor 418, and an accelerometer 419. In practice, an IMD may also utilize a sensor for determining cardiac conduction time, temperature sensors, blood pH sensors, and/or other known data sources. The various data sources 412 may be provided alone or in any combination with each other, and may vary widely from embodiment to embodiment.

RVDP sensor 418 is suitably configured to measure the real-time RVDP of the patient's heart and to provide raw RVDP data to data collection module 402. In turn, data collection module 402 and/or data processing module 404 can convert the raw RVDP data into a usable RVDP signal for analysis as described herein. A practical IMD can utilize any suitable RVDP sensor 418, including, without limitation:

RVDP sensors that are mounted through the wall of the heart; RVDP sensors that utilize structures of the heart as a transducer membrane; and RVDP sensors that are inserted through appendages or through cardiac valves. Indeed, processor architecture 400 can be configured to accommodate the specific RVDP signal format and characteristics associated with the particular RVDP sensor or sensors deployed with the IMD.

The accelerometer 419 can be connected to the IMD 100 by lead wires and designed to be affixed to walls of the left atrium, right ventricle, or left ventricle in order to detect mechanical contractions of those chambers. In an exemplary implementation, the accelerometer lead wires are advanced to the heart intravenously. A right ventricular accelerometer may be affixed to the endocardial surface of the right ventricle at the septal wall, while left atrial and ventricular accelerometers may be placed in the coronary sinus and cardiac veins, respectively, to sense movement of the free walls of those chambers. The accelerometer 419 can be interfaced to the data processing module 404 by the data collection module 402.

The data collection module 402 suitably receives data from each of the data sources 412 by polling each of the data sources 412, by responding to interrupts or other signals generated by the data sources 412, by receiving data at regular time intervals, or according to any other temporal scheme. In particular, the data collection module 402 is configured to obtain a RVDP signal from the patient for processing. Data may be received at the data collection module 402 in digital or analog format according to any protocol. If any of the data sources 412 generate analog data, the data collection module 402 suitably translates the analog signals to digital equivalents using any form of analog-to-digital conversion scheme presently known or subsequently developed. The data collection module 402 may also convert data from protocols used by the data sources 412 to data formats acceptable to the data processing module 404, as appropriate. It should be appreciated that the RVDP sensor 418, the processor architecture 400, the data collection module 402, and any corresponding logical elements, individually or in combination, are example means for obtaining a RVDP signal of a patient as used herein.

The data processing module 404 is any circuit, programming routine, application or other hardware/software module that is capable of processing data received from the data collection module 402. In various embodiments, the data processing module 404 is a software application executing on processor architecture 400 to implement the processes described below. Accordingly, the data processing module 404 interprets received RVDP signals 300, generates or analyzes signals based upon or derived from received RVDP signals 300, and/or handles other data to adjust one or more operating parameters of the IMD 100.

In an exemplary embodiment, the data processing module 404 receives RVDP signal data and/or other appropriate information from the data collection module 402 and interprets the data using conventional digital signal processing techniques. For example, the data processing module 404 may generate a secondary signal 302 that is based upon the first derivative of the RVDP signal (such a secondary signal 302 may be referred to herein as a RV dP/dt signal as depicted in FIG. 3). In this regard, the data processing module 404, the processor architecture 400, and any corresponding logical elements, individually or in combination, are example means for generating secondary signals 302 based upon the RVDP signal 300.

As described in more detail below, the data processing module 404 is configured to identify at least one attribute of the RVDP signal 300, and/or at least one attribute of a secondary signal 302 based upon the RVDP signal 300, and correlate the identified attributes to a hemodynamic status or cardiac performance of the patient. In this manner, the RVDP signal 300 data can be utilized as a feedback control mechanism to adjust the therapy delivered by the IMD 100. It should be appreciated that the data processing module 404, the processor architecture 400, and any corresponding logical elements, individually or in combination, are example means for identifying attributes of the RVDP signal 300 and/or the RV dP/dt signal 302.

The communication module 410 is any circuit or routine that facilitates the transfer of data, information, reports, or programming instructions between the IMD 100 and an external device, system, or person (e.g., the patient, a physician, or a caregiver). In various embodiments, communication module 410 may be configured to generate an audible or visible alarm 420, handle wireless messages via a telemetry circuit 422, or manage the transmission of other data using any suitable interface 424. In this regard, the communication module 410 may facilitate open-loop feedback control of the IMD operating parameters by transmitting RVDP signals 300 or RVDP signal attributes to an external processing system that responds with programming instructions to adjust the AV delay or other IMD parameters in the manner described herein. In some embodiments, the alarm 420 and/or the telemetry module 422 can be used to provide a warning feature for disease progression, cardiac reserve, exercise tolerance, and/or congestive cardiac failure.

The therapy module 408 is any suitable circuit, software application or other component that is configured to deliver cardiac therapy 426 to the patient. In the example embodiment, the therapy module 408 is configured to provide an optimized pacing heart rate as one form of cardiac therapy 426. In some embodiments, therapy module 408 may be alternatively or additionally configured to deliver various modes of pacing, post-extrasystolic potentiation, cardioversion, defibrillation and/or any other therapy. It should be appreciated that the therapy module 408, the cardiac therapy 426, the processor architecture 400, and any corresponding logical elements, individually or in combination, are example means for automatically optimizing the pacing heart rate of the therapy signal generated by the IMD 100.

The various components and processing modules of the IMD 100 may be housed in a common housing such as that shown in FIG. 1. Alternatively, portions of the IMD 100 may be housed separately. For example, portions of the therapy module 408 could be integrated with the IMD 100 or provided in a separate housing. In this case, the therapy module 408 may interact with therapy electrodes via an electrical cable, wireless link, or the interface 424.

Figure 5:
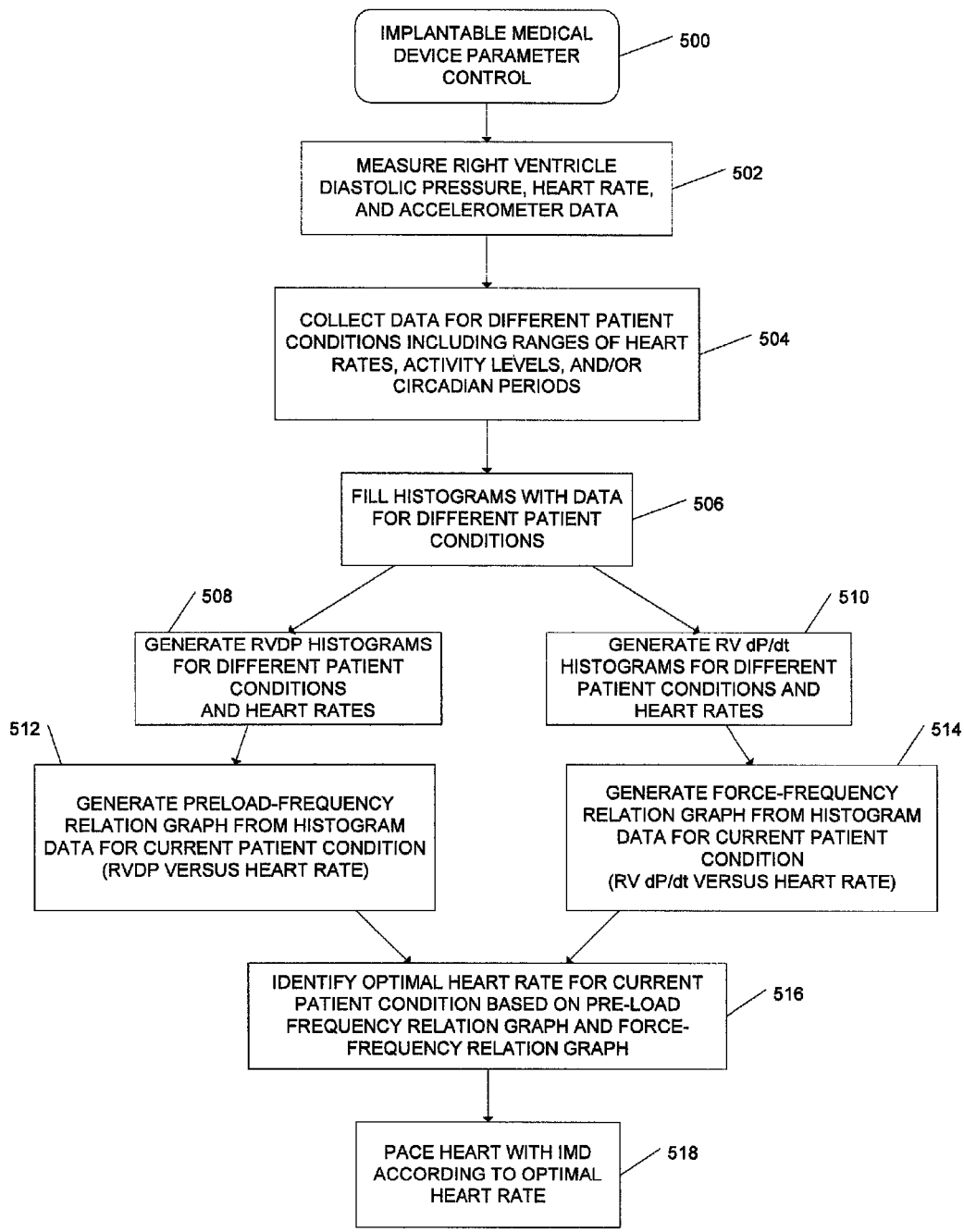
FIG. 5 is a flow diagram of an IMD parameter control process, which may be performed by an IMD configured in accordance with an embodiment of the present disclosure.

FIG. 5 is a flow diagram of an IMD parameter control process 500, which may be performed by an IMD 100 configured in accordance with an example embodiment of the present disclosure. The various tasks performed in connection with process 500 may be performed by software, hardware, firmware, or any combination thereof. For illustrative purposes, the following description of process 500 may refer to elements mentioned above in connection with FIGS. 1-4. In practical embodiments, portions of process 500 may be performed by different elements of the described system, e.g., data sources 412, processor architecture 400, or any component thereof. It should be appreciated that process 500 may include any number of additional or alternative tasks, the tasks shown in FIG. 5 need not be performed in the illustrated order, and process 500 may be incorporated into a more comprehensive procedure or process having additional functionality not described in detail herein.

IMD parameter control process 500 represents a method for analyzing a patient's RVDP data and optimizing a pacing heart rate provided by the IMD 100. Process 500 includes measuring RVDP, heart rate, and accelerometer data (task 502). Process 500 includes collecting data for different patient conditions, including ranges of heart rates, activity levels, and/or circadian periods, such as day-time or night-time (task 504). For example, data can be collected for an extended time period, such as 14 months, with a suitable monitoring device, such as the CHRONICLE® monitoring device available from Medtronic, Inc. of Minneapolis, Minn. In some embodiments, the CHRONICLE® monitoring device can be used to obtain the RVDP signals 300, to extract the secondary signal 302 for RV dP/dt, to obtain heart rate, and to obtain accelerometer data per beat.

Figure 6A:
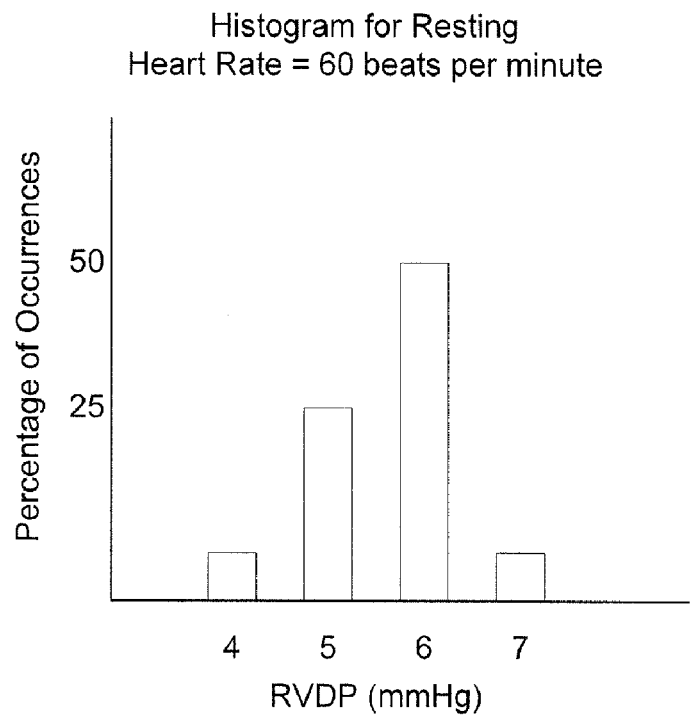
FIGS. 6A-6B are examples of histograms for RVDP at resting heart rates.
Figure 6B:
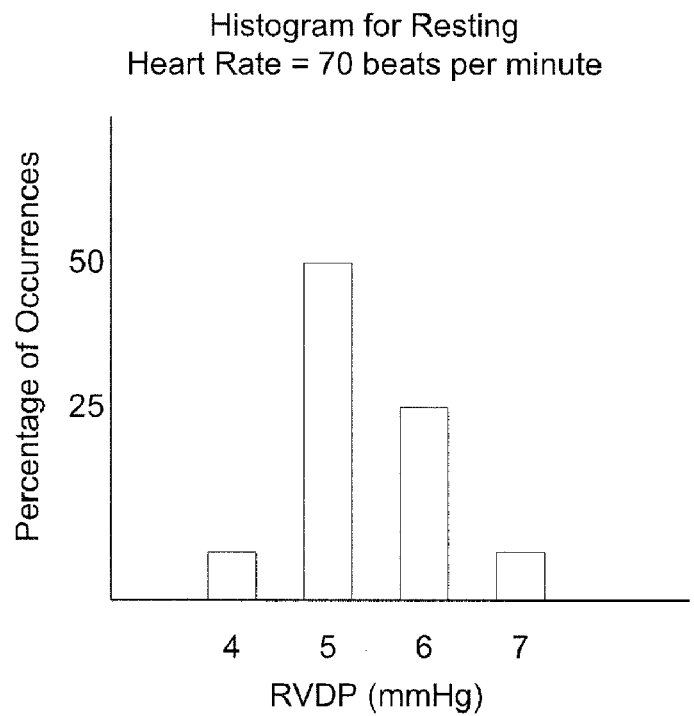

Histograms can be filled with the data collected for the patient during the extended time period (task 506). Histograms can be filled with data representing different heart rate ranges and activity conditions based on the accelerometer data. A histogram corresponding to each patient condition and each heart rate can be created for the patient's RVDP data. For example, as shown in FIGS. 6A and 6B, a histogram of RVDP data can be created for a resting heart rate of 60 beats per minute and a histogram of RVDP data can be created for a resting heart rate of 70 beats per minute, respectively. In other words, the RVDP data for the extended time period can be summarized in a histogram for each heart rate (task 508). The histograms can then be used to identify the RVDP value that has the highest percentage of occurrences during the extended time period for each particular heart rate (e.g., a RVDP of 6 mmHg occurs 50% of the time at 60 beats per minute, as shown in FIG. 6A, while a RVDP of 5 mmHg occurs 50% of the time at 70 beats per minute, as shown in FIG. 6B). A typical range for RVDP is 0-8 mmHg (without reference to atmospheric pressure).

Figure 7A:
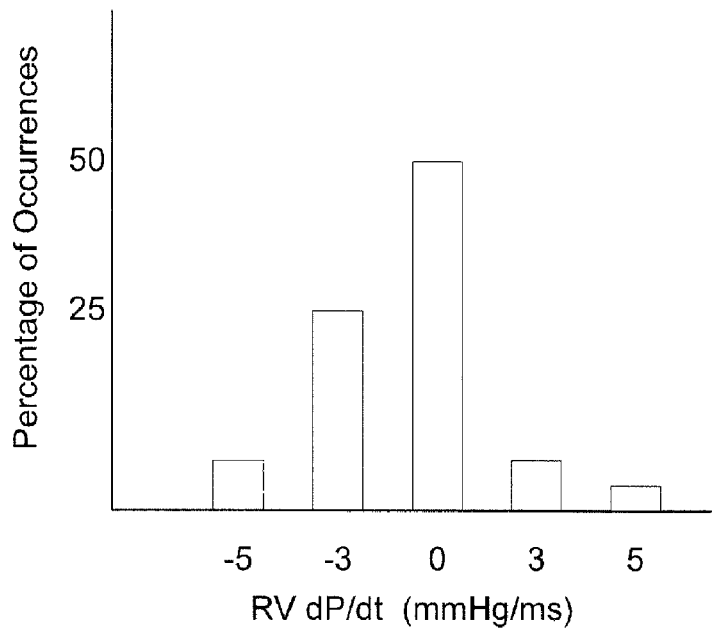
FIGS. 7A-7B are examples of histograms for RV dP/dt at resting heart rates.
Figure 7B:
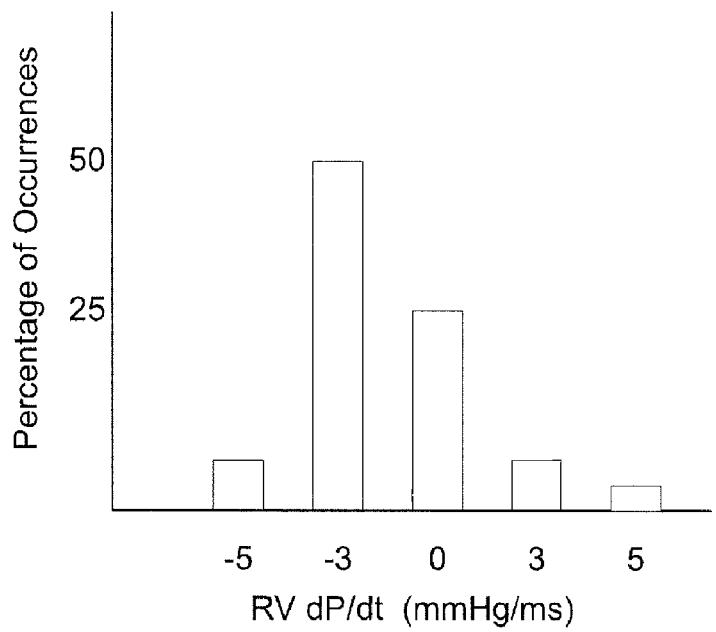
Figure 8A:
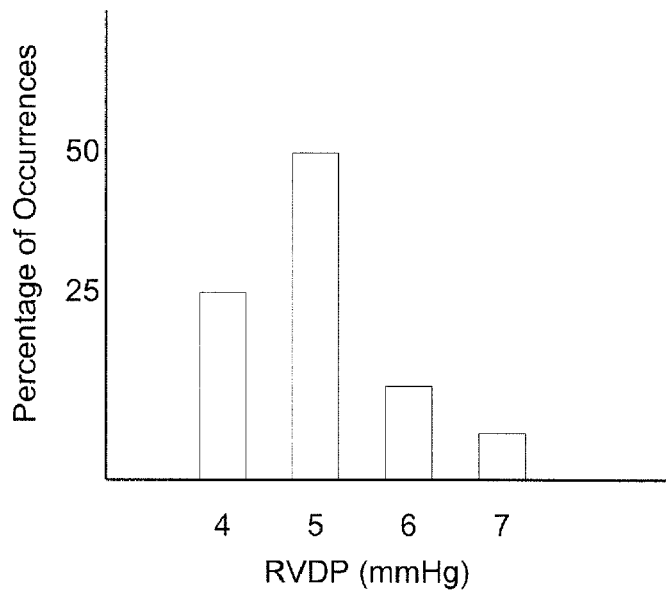
FIG. 8A-8B are examples of histograms for RVDP at exercise heart rates.
Figure 8B:
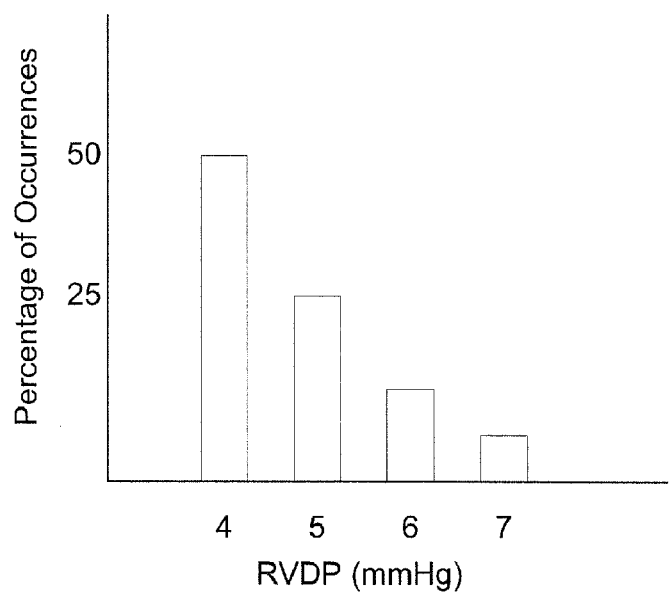
Figure 9A:
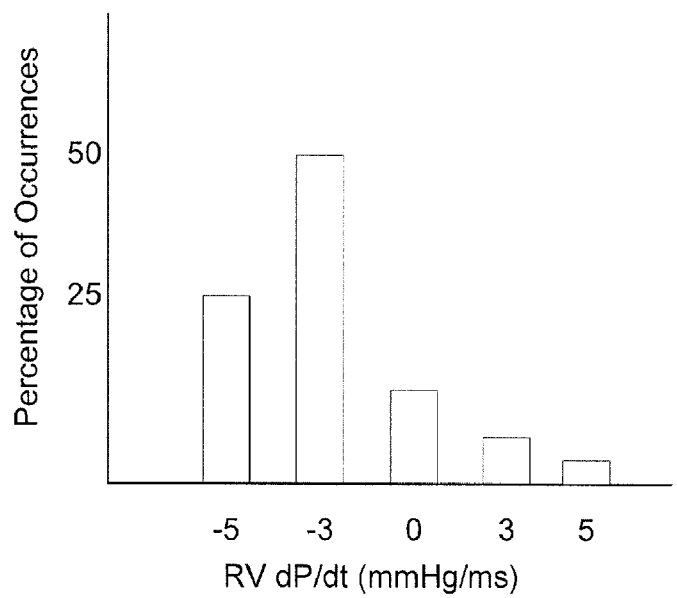
FIG. 9A-9B are examples of histograms for RV dP/dt at exercise heart rates.
Figure 9B:
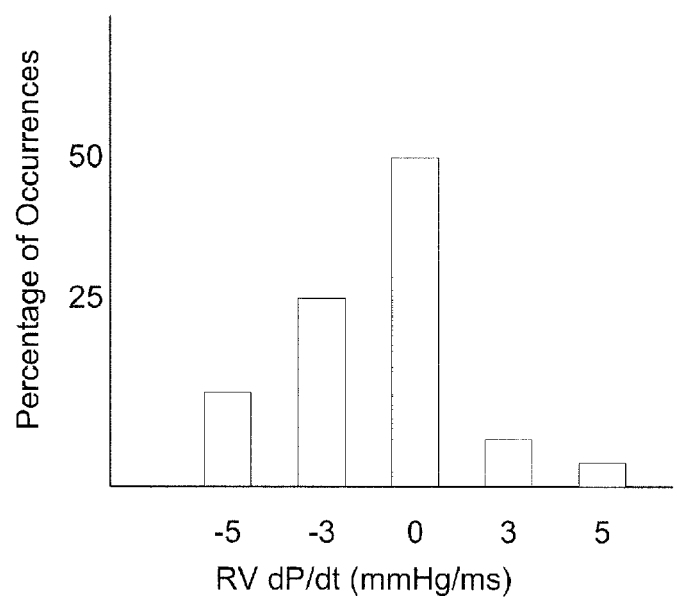

Similarly, histograms can be generated for the first derivative RV dP/dt (task 510). For example, as shown in FIGS. 7A and 7B, a histogram of RV dP/dt data can be created for a resting heart rate of 60 beats per minute and a histogram of RV dP/dt data can be created for a resting heart rate of 70 beats per minute, respectively. The histograms can then be used to identify the RV dP/dt value that has the highest percentage of occurrences during the extended time period for each particular heart rate (e.g., a RV dP/dt of 0 mmHg/ms occurs 50% of the time at 60 beats per minute, as shown in FIG. 7A, while a RV dP/dt of −3 mmHg/ms occurs 50% of the time at 70 beats per minute, as shown in FIG. 7B). The RVDP and RV dP/dt histograms can also be created for a patient condition in which the patient is exercising (e.g., at a heart rate of 120 or 130 beats per minute), as shown in FIGS. 8A-9B.

In some embodiments, the data for the histograms can be based on information that is stored in the memory 106 of the IMD 100 and subsequently re-arranged into blocks that represent the specific patient conditions based on the heart rate or accelerometer data. In some embodiments, the data for the histograms can be stored from test periods during stable patient conditions reflecting the desired patient condition that needs to be optimized (e.g., previous stable resting conditions can be used to optimize future resting conditions and previous stable exercise conditions can be used to optimize future exercise conditions).

Although only two examples of patient conditions and corresponding histograms are shown and described herein, any suitable number of RVDP and RV dP/dt histograms can be created for as many patient conditions as desired. The histograms can be categorized according to suitable patient conditions, such as rest exercise, fluid-overload, day-time, night-time, etc. The various patient conditions can be based on data from the heart rate monitor 416 and/or data obtained from the accelerometer 419, as shown in FIG. 4. The accelerometer 419 can generate data regarding whether the patient is lying down, standing, or moving while the RVDP, heart rate, and/or ECG data is being gathered by the cardiac sensors and sources 412.

Figure 10:
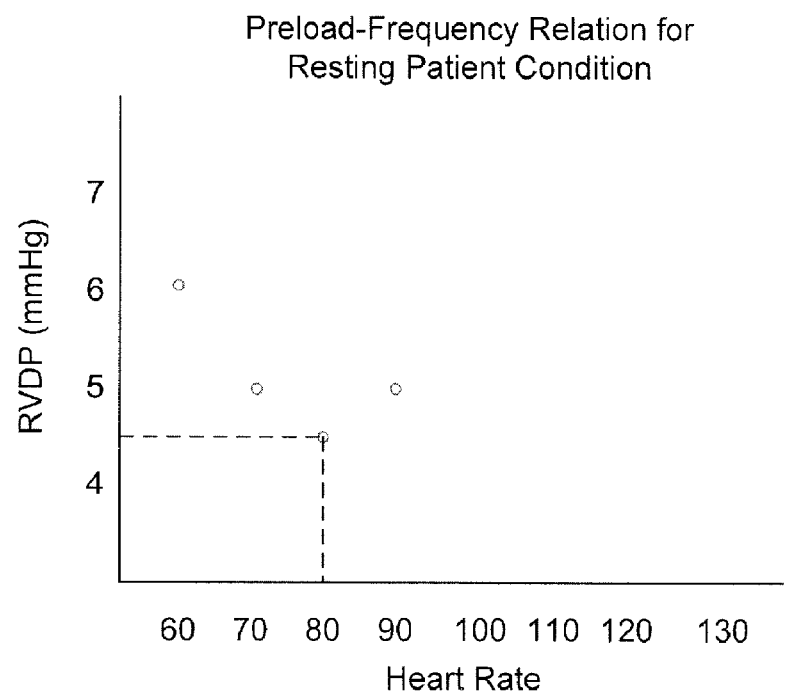
FIG. 10 is a preload-frequency relation graph for a resting patient condition.
Figure 12:
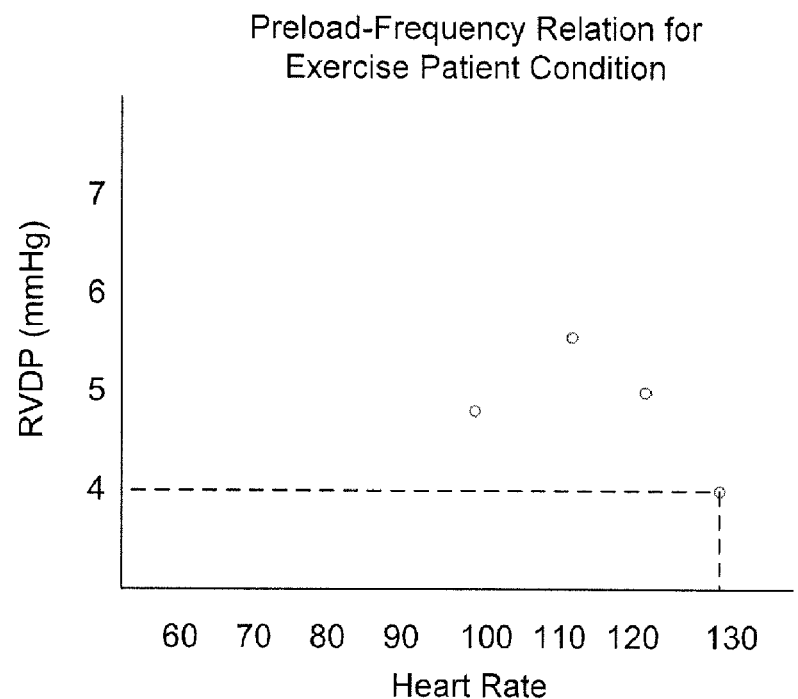
FIG. 12 is a preload-frequency relation graph for an exercise patient condition.

Using the RVDP histograms, a preload-frequency relation graph can be generated for a particular patient condition (task 512). As shown in FIGS. 10 and 12, graphs can be created using data points representing the RVDP with the highest percentage of occurrences for a particular heart rate (i.e., a graph of highest occurrence RVDP values versus heart rate values). Using the preload-frequency relation graph of FIG. 10 or FIG. 12 depending on the patient's current activity level, a first heart rate can be identified that corresponds to the optimal minimum RVDP (or the estimate of an optimal diastolic pulmonary artery pressure) for the cardiac preload condition. This heart rate can be the heart rate on the graph of FIG. 10 where the minimum pressure occurs.

Figure 11:
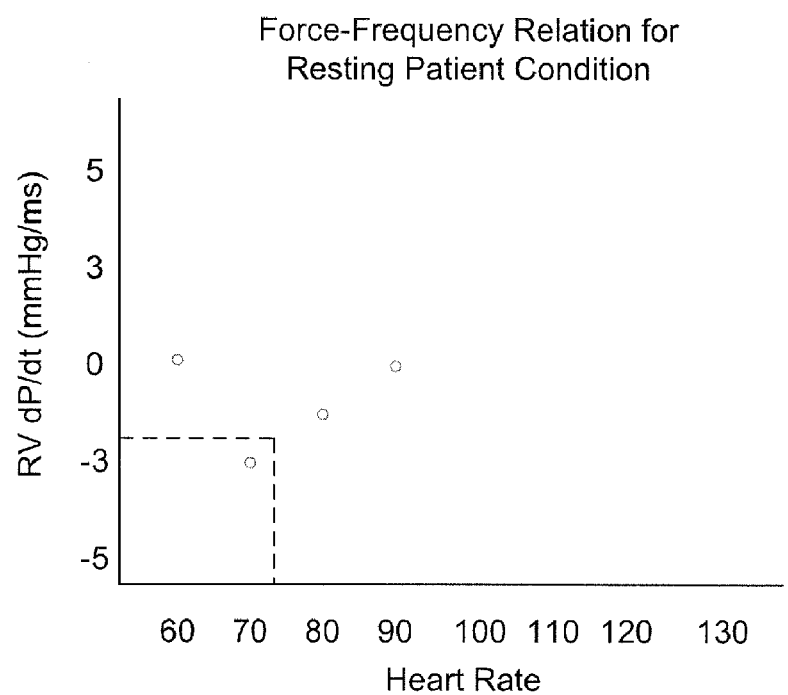
FIG. 11 is a force-frequency relation graph for a resting patient condition.
Figure 13:
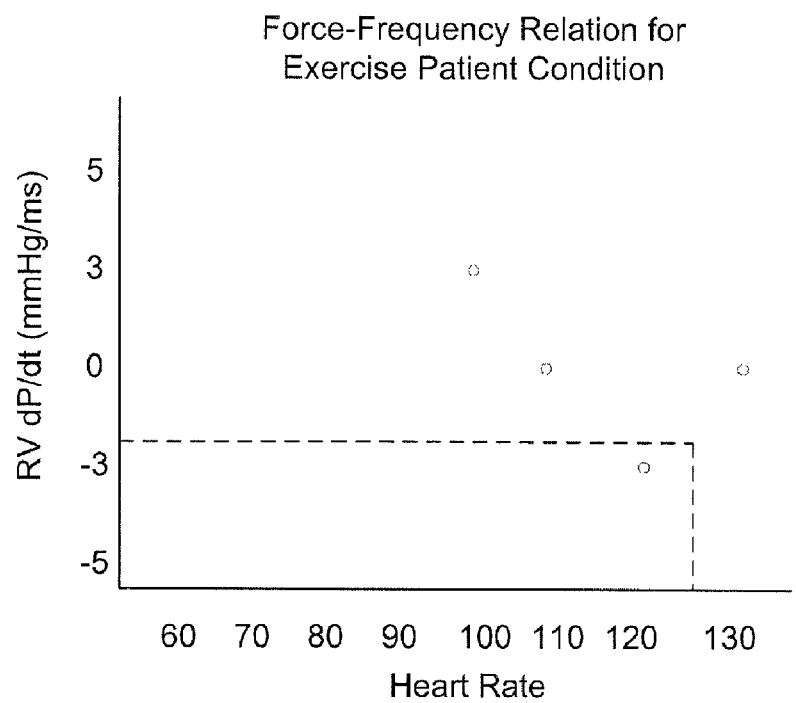
FIG. 13 is a force-frequency relation graph for an exercise patient condition.

Using the RV dP/dt histograms, a force-frequency relation graph can also be generated for a particular patient condition (task 514). As shown in FIGS. 11 and 13, graphs can be created using data points representing the RV dP/dt with the highest percentage of occurrences for a particular heart rate (i.e., a graph of highest occurrence RV dP/dt values versus heart rate values). Using the force-frequency relation graph of FIG. 11 or FIG. 13 depending on the patient's current activity level, a second heart rate can be identified that corresponds to the point of the curve representing the upstroke in dP/dt versus heart rate (i.e., a heart rate that achieves sustained ionotropic reserve which can correspond to the steepness of the pressure increase during systole).

An optimized pacing heart rate according to which the IMD 100 should pace the heart 102 can be identified between the first heart rate taken from the preload-frequency relation graph of FIG. 10 or FIG. 12 and the second heart rate taken from the force-frequency relation graph of FIG. 11 or FIG. 13 (task 516). In this manner, an optimization of pacing heart rates can lead to optimized pre-load conditions while sustaining the ionotropic reserve of the heart 102 and the ability to modulate the heart rate by the neuro-hormonal system.

Digital data analysis can be performed to generate curves corresponding to the data of FIGS. 10-13. In some embodiments, the digital data analysis can include performing multi-dimensional polygonal fitting and/or using waveform algorithms to generate a curve for the data based on rules for each patient condition. The waveform algorithms can be similar to trigger algorithms used for ECG analysis or the Simpson's Rule method (in which the volume is divided into slices and the slices are summed in order to determine the whole).

If the patient is experiencing a fluid-overload condition, the optimized heart rate can be the heart rate at the point in the force-frequency relation graph representing the upstroke in the dP/dt versus heart rate curve based on the resting heart rate histograms. For the patient's ability to perform exercise, the optimized heart rate can be the heart rate at the point in the force-frequency relation graph representing the highest offset in the dP/dt versus heart rate curve based on the exercise heart rate histograms.

The IMD 100 can then pace the heart 102 according to the optimized pacing heart rate (task 518). In some embodiments, the process 500 is a closed-loop feedback control scheme performed by the IMD 100 in which the process 500 can return to tasks 512 and 514 or other previous tasks after performing task 518 in order to identify a new optimized pacing heart rate when the patient's current condition changes (e.g., the patient condition changes from resting to exercising).

In accordance with the example embodiment of the present disclosure, task 516 is associated with optimizing the pacing heart rate of a dual-chamber pacing device. Of course, task 516 may additionally (or alternatively) adjust other IMD parameters, including, without limitation: AV delay timing; Vv delay timing, which is the delay between pacing of both ventricles; AA delay timing, which is the delay between pacing of both atria; intra-atrium pacing delays for IMDs supporting multiple pacing leads in an atrium; intra-ventricle pacing delays for IMDs supporting multiple pacing leads in a ventricle; heart rate; lead location selection for IMDs supporting configurable activation of a plurality of leads in a single chamber (either the atrium and ventricle), which includes both therapy delivery and sensing leads. The IMD 100 can adjust the hemodynamic parameter or parameters (or can maintain its current operating status) in response to the RVDP and/or RV dP/dt analysis. Of course, the specific adjustment mode, amount of adjustment, and frequency of adjustment will depend upon the current status of the patient, and the particular performance specifications of the IMD 100 itself.

While at least one example embodiment has been presented in the foregoing detailed description, it should be appreciated that a vast number of variations exist. It should also be appreciated that the example embodiment or embodiments described herein are not intended to limit the scope, applicability, or configuration of the present disclosure in any way. Rather, the foregoing detailed description will provide those skilled in the art with a convenient road map for implementing the described embodiment or embodiments. It should be understood that various changes can be made in the function and arrangement of elements without departing from the scope of the present disclosure as set forth in the appended claims and the legal equivalents thereof.

The invention claimed is:

1. A pacing implantable medical device comprising:
    a data collection module configured to obtain a pressure signal and a heart rate signal;
    a data processing module coupled to the data collection module,
        the data processing module configured to generate a preload-frequency relation and a force-frequency relation from histogram data for a patient condition,
        the data processing module configured to determine an optimal pacing heart rate for the patient condition, the optimal pacing heart rate being substantially between a first heart rate corresponding to a minimum preload condition based on the preload-frequency relation and a second heart rate corresponding to a sustained ionotropic reserve condition based on the force-frequency relation; and
    a therapy module coupled to the data processing module, the therapy module configured to provide the optimal pacing heart rate.

2. The device of claim 1 wherein the pressure signal is a right ventricle diastolic pressure signal.

3. The device of claim 1 wherein the therapy module provides cardiac resynchronization therapy.

4. The device of claim 1 wherein the preload-frequency relation is a first curve of right ventricular diastolic pressure versus heart rate; and wherein the force-frequency relation is a second curve of a first derivative of right ventricular diastolic pressure versus heart rate.

5. The device of claim 4 wherein the minimum preload condition is a minimum heart rate on the first curve.

6. The device of claim 4 wherein the sustained ionotropic reserve condition is an upstroke in the second curve.

7. The device of claim 2 wherein the data collection module collects the right ventricular diastolic pressure signal for an extended time period before generating the histogram data for the patient condition.

8. The device of claim 1 and further comprising generating a plurality of histograms for each one of a plurality of patient conditions.

9. The device of claim 8 wherein the plurality of patient conditions includes at least two of resting, exercise, fluid-overload, day-time, and night-time.

10. The device of claim 1 and further comprising obtaining accelerometer data and generating a plurality of histograms representing each one of a plurality of patient conditions including different activity levels based on the accelerometer data.

11. The device of claim 1 wherein the patient condition is a resting fluid-overload condition; and wherein the optimal pacing heart rate is a heart rate representing an upstroke in the second curve.

* * * * *